US012364400B2

(12) United States Patent
Nicholson et al.

(10) Patent No.: US 12,364,400 B2
(45) Date of Patent: Jul. 22, 2025

(54) WEARABLE BIOSENSOR DEVICES WITH ADAPTIVE POWER CONSUMPTION

(71) Applicant: Verily Life Sciences LLC, South San Francisco, CA (US)

(72) Inventors: Charles Nicholson, Concord, MA (US); David He, San Mateo, CA (US); Brian Schiffer, San Francisco, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 618 days.

(21) Appl. No.: 17/457,504

(22) Filed: Dec. 3, 2021

(65) Prior Publication Data

US 2022/0183574 A1 Jun. 16, 2022

Related U.S. Application Data

(60) Provisional application No. 63/199,159, filed on Dec. 10, 2020.

(51) Int. Cl.
| | |
|---|---|
| *A61B 5/0205* | (2006.01) |
| *A61B 5/00* | (2006.01) |
| *G06F 1/3206* | (2019.01) |
| *H04W 4/38* | (2018.01) |
| *H04W 4/80* | (2018.01) |

(52) U.S. Cl.
CPC ........ *A61B 5/02055* (2013.01); *A61B 5/0026* (2013.01); *A61B 5/6823* (2013.01); *G06F 1/3206* (2013.01); *H04W 4/38* (2018.02); *H04W 4/80* (2018.02)

(58) Field of Classification Search
CPC ............... A61B 5/0026; A61B 5/6823; A61B 2560/0204; A61B 5/6802; G06F 1/3206; G06F 1/163; G06F 1/3287; H04W 4/38; H04W 4/80
See application file for complete search history.

(56) References Cited

U.S. PATENT DOCUMENTS

| | | | |
|---|---|---|---|
| 6,992,580 B2 | 1/2006 | Kotzin et al. | |
| 8,922,376 B2 | 12/2014 | Kangas et al. | |
| 9,665,762 B2 | 5/2017 | Thompson et al. | |
| 10,104,458 B2 | 10/2018 | Boesen et al. | |

(Continued)

OTHER PUBLICATIONS

Pedram et al., "Resource-Efficient Wearable Computing for Real-Time Reconfigurable Machine Learning: A Cascading Binary Classification", 2019 IEEE 16th International Conference on Wearable and Implantable Body Sensor Networks (BSN). IEEE, 2019.

(Continued)

*Primary Examiner* — Omeed Alizada
(74) *Attorney, Agent, or Firm* — Kilpatrick Townsend & Stockton LLP (57) ABSTRACT

One disclosed example method includes receiving sensor data from a biosensor; determining an event using a first analysis based on the sensor data, the first analysis having a first power cost; determining to perform a second analysis based on the event; in response to determining to perform the second analysis, performing the second analysis based on the sensor data, the second analysis having a second power cost greater than the first power cost; and wirelessly transmitting results of the second analysis to a remote device.

27 Claims, 7 Drawing Sheets (56) References Cited

U.S. PATENT DOCUMENTS

| | | | | |
|---|---|---|---|---|
| 2009/0030279 A1* | 1/2009 | Zander | ................... | A61B 5/073 |
| | | | | 600/118 |
| 2013/0137946 A1* | 5/2013 | Geske | ................ | A61B 5/14552 |
| | | | | 600/323 |
| 2014/0108842 A1* | 4/2014 | Frank | ................... | G06F 1/3212 |
| | | | | 713/323 |
| 2015/0150481 A1* | 6/2015 | Gazdzinski | .......... | A61B 6/4258 |
| | | | | 604/285 |
| 2016/0009807 A1 | 1/2016 | Govindappa et al. | | |

OTHER PUBLICATIONS

Vaquerizo-Hdez et al., "A low power consumption algorithm for efficient energy consumption in zigbee motes", Sensors 17.10 (2017): 2179.

International Application No. PCT/US2021/061824, International Search Report and the Written Opinion, Mailed On Feb. 23, 2022, 11 pages.

\* cited by examiner

WEARABLE BIOSENSOR DEVICES WITH ADAPTIVE POWER CONSUMPTION

CROSS-REFERENCE TO RELATED APPLICATIONS

This application claims priority to U.S. Provisional Patent Application No. 63/199,159, filed Dec. 10, 2020, titled "Wearable Biosensor Devices With Adaptive Power Consumption," the entirety of which is hereby incorporated by reference.

FIELD

The present application generally relates to wearable biosensors and more specifically relates to wearable biosensor devices with adaptive power consumption.

BACKGROUND

Sensing physiological information can be useful to detect parameters such as breathing rate, pulse rate, blood pressure, etc. Such physiological information is often captured in a doctor's office by trained medical personnel or using specialized equipment. In some cases, sensors may be affixed to a person to detect certain information that may be used to determine different physiological parameters. Wearable devices such as smartwatches or continuous glucose monitors can be used to detect some such physiological parameters outside of a doctor's office.

SUMMARY

Various examples are described for wearable biosensor devices with adaptive power consumption. One example method includes receiving sensor data from a biosensor; determining an event using a first analysis based on the sensor data, the first analysis having a first power cost; determining to perform a second analysis based on the event; in response to determining to perform the second analysis, performing the second analysis based on the sensor data, the second analysis having a second power cost greater than the first power cost; and wirelessly transmitting results of the second analysis to a remote device.

One example device includes a biosensor; a radio subsystem; a non-transitory computer-readable medium; and a processor communicatively coupled to the biosensor, the radio subsystem, and the non-transitory computer-readable medium, the processor configured to execute processor-executable instructions stored in the non-transitory computer-readable medium to: receive sensor data from a biosensor; determine an event using a first analysis based on the sensor data, the first analysis having a first power cost; determine to perform a second analysis based on the event; in response to a determination to perform the second analysis, perform the second analysis based on the sensor data, the second analysis having a second power cost greater than the first power cost; and wirelessly transmit, using the radio subsystem, results of the second analysis to a remote device.

One example non-transitory computer-readable medium includes processor-executable instructions configured to cause a processor to receive sensor data from a biosensor; determine an event using a first analysis based on the sensor data, the first analysis having a first power cost; determine to perform a second analysis based on the event; in response to a determination to perform the second analysis, perform the second analysis based on the sensor data, the second analysis having a second power cost greater than the first power cost; and wirelessly transmit, using the wireless transmitter, results of the second analysis to a remote device.

Another example method includes receiving sensor data from a biosensor; determining an event using an analysis based on the sensor data; determining to transmit the sensor data to a remote device; in response to determining to transmit the sensor data to a remote device, activating a radio subsystem; wirelessly transmitting, using the radio subsystem, results of the second analysis to a remote device; and deactivating the radio subsystem.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of wearable biosensor devices with adaptive power consumption. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

A person may use a wearable biosensor to gather information about a particular physiological measurement over time, such as breathing rate, pulse rate, pulse rhythm, oxygen saturation (e.g., $SpO_2$), blood pressure, glucose or other analyte levels, etc. The biosensor may perform measurements over time and allow a remote device to obtain the measurements at any convenient time. However, some biosensor devices may enable more complex data analysis than simply collecting data for later download. For example, a biosensor may include an accelerometer that outputs data indicating acceleration values in one or more degrees of freedom. While some biosensors may simply record such accelerometer information, others may perform more complex analysis, such as determining steps, gait, energy expenditure, etc. But such complex analysis typically consumes more power than simply receiving and storing sensor data. In addition, some sensors may consume significant amounts of power when operating at a high sampling rate or otherwise providing high fidelity data.

To reduce power consumption, an example biosensor device can dynamically adjust sensor data analysis to reduce analysis complexity based on received sensor data. In addition, the biosensor device can adjust the operating mode of the biosensor itself, such as by adjusting a sampling rate or fidelity, and it can determine whether wireless data transfer should be used to report sensor data to a remote device. Power consumption for this example device is a significant concern because it is a hermetically sealed device and its battery cannot be changed. Instead, it is designed to operate for a period of time and then be discarded. To help prolong the device's useful life, it avoids consuming battery power unnecessarily. For example, running a sensor, e.g., an accelerometer, at its full sampling rate with high-fidelity data output may drain the device's battery in a matter of days, rather than an intended useful life of weeks or months. Further, if the biosensor continuously maintains a wireless connection with a remote device, e.g., using Bluetooth, it may expend significant amounts of power simply maintaining the Bluetooth connection but without actually communicating any data or communicating data that indicates uninteresting events, such as very little movement occurring when the user is sleeping. To avoid such unnecessary power consumption the device can adjust the operating mode one or more biosensors, and avoid high-complexity/high-power processing unless the data indicates such processing may be desirable. Further, the device can deactivate its wireless capabilities except when sufficiently urgent information needs to be transmitted to a remote device, such as to the user or a medical provider.

In this example, the example biosensor device measure the wearer's pulse using an optical photoplethysmography ("PPG") sensor. In a reduced power state, the biosensor device configures the PPG sensor to sample data at a rate of 50 samples per second (Hz) and to output 8-bit samples. The biosensor's processor receives the incoming PPG data and performs low-complexity processing to determine a pulse rate and inter-beat-interval ("IBI"). These values are compared against different thresholds and, if the thresholds are not met, the biosensor remains in its reduced power state. However, if one of the thresholds is met, the biosensor device commands the PPG sensor to increase a sampling rate to 1000 Hz and to output 12-bit samples. By increasing the sampling rate and data rate, the PPG sensor's power consumption will increase substantially. In addition, because more data is received from the PPG sensor, the processor will consume more power.

In addition to increasing the sampling rate, the processor also executes one or more algorithms to determine whether the wearer is experiencing arrhythmia or another cardiac event. These algorithms involve complex processing of the received sensor data and thus involve significant processor utilization, e.g., utilization above 80-90%, causing increased power consumption. If the processing determines an arrhythmia or other cardiac event has occurred, the processor determines whether the event is urgent enough to warrant activating a radio subsystem to transmit information to a remote device, thereby consuming additional power. If the data is transmitted to a remote device, the biosensor can then deactivate the radio subsystem to conserve power until the next time it is needed.

Using such techniques, example wearable biosensor devices can operate for extended periods of time, e.g., multiple months, despite being deployed with relatively small, non-replaceable batteries. Such devices may provide continuous monitoring of certain physiological parameters, e.g., pulse, at relatively low power levels, while being capable of detecting more significant physiological events and wirelessly reporting them off-device. Thus, examples biosensor devices according to this disclosure may enable a wearer to need to replace monitoring devices infrequently, reducing impact on the wearer and reducing overall costs to monitor the wearer.

This illustrative example is given to introduce the reader to the general subject matter discussed herein and the disclosure is not limited to this example. The following sections describe various additional non-limiting examples and examples of wearable biosensor devices with adaptive power consumption.

Figure 1:
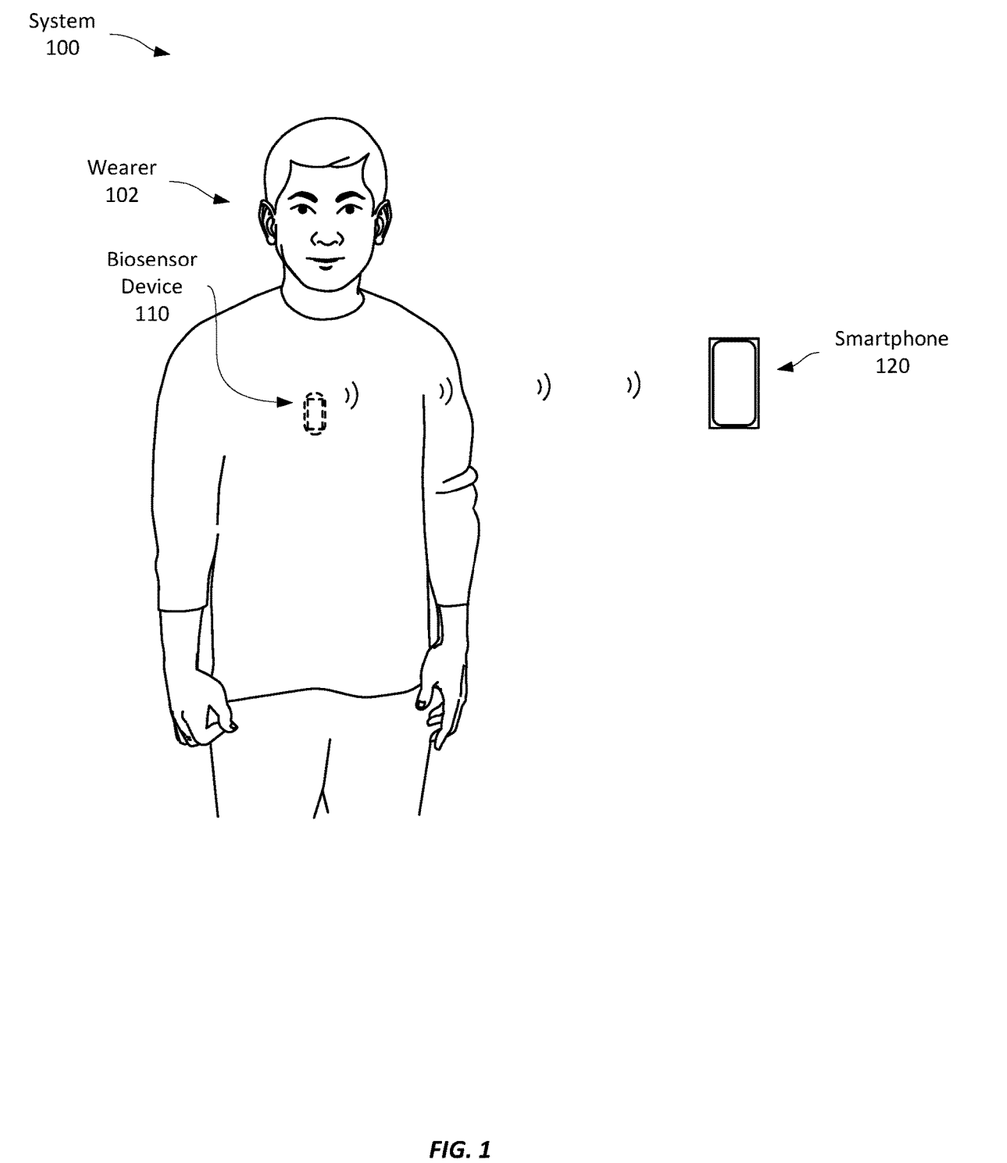
FIGS. 1 and 2 show example systems including wearable biosensor devices with adaptive power consumption.

Referring now to FIG. 1, FIG. 1 shows an example system 100 including a wearable biosensor device 110 and a smartphone 120. The biosensor device 110 in this example is worn on the wearer's chest, under their clothes and it monitors cardiac activity, such as heart rate and heart rhythm. The biosensor device 110 uses a biosensor to sense the cardiac activity and transmits sensor readings to the biosensor device's processor, which stores the data in memory in the biosensor device 110. The processor executes a computationally simple process to determine heart rate and rhythm and stores the determined data in memory along with the raw sensor data. It may perform such calculations after some number of sensor samples have been received or periodically based on elapsed time, etc.

After determining heart rate and rhythm information, the biosensor device 110 may then determine whether that information indicates that additional processing should be performed, such as to determine an arrhythmia or other cardiac event. To do so, the processor may determine whether the heart rate or rhythm are within a normal range for the wearer. If so, the processor continues to determine the wearer's heart rate and rhythm based on received biosensor data, but does not perform more complex processing on the received data.

However, the processor determines that the wearer's heart rate or rhythm are outside of the normal range for the wearer, the processor may perform additional processing to identify any potential cardiac events. To do so, the processor may process previously obtained biosensor data or it may wait to obtain additional biosensor data. The processor may also command the biosensor to increase its sampling rate or increase the resolution of the sensed data, such as by reporting 16- or 32-bit values rather than 8- or 16-bit values, respectively, or by sensing additional parameters. After obtaining any additional information, the processor may execute the complex algorithm to attempt to identify any cardiac events. This additional processing may include computationally expensive processing that involves significant processing or memory utilization, thereby increasing power consumption.

After identifying any potential cardiac events, the processor determines the urgency of those cardiac events and, if any are sufficiently urgent, sends a notification to the smartphone 120, thereby alerting the wearer 102 or causing the smartphone 120 take action, e.g., contacting emergency services. If any of the cardiac events is sufficiently urgent, the processor activates the biosensor device's radio to wirelessly transmit information to the smartphone 120. In this example, the biosensor device 110 establishes a low-power Bluetooth ("BLE") connection to the smartphone 120 and transfers data to the smartphone 120 using that connection. After the data is successfully transferred, the processor de-activates the radio.

In the scenario discussed above, the biosensor device 110 typically only consumes power through steady-state sensing and low-power processing of the incoming biosensor data, thereby avoiding performing high-computational-complexity processing that might not be warranted at most times, e.g., the wearer suffers from a mild cardiac arrhythmia and ordinarily experiences regular heart beats and rhythms. Performing arrhythmia detection continuously on incoming biosensor data may rapidly consume the biosensor device's battery, despite only rarely detecting arrhythmia events. Similarly, maintaining a continuous BLE connection with the smartphone 120 itself may cause significant battery drain, irrespective of any processing performed by the processor. Thus, the biosensor device 110 is able to operate with low power consumption most of the time and only allocating increased power when biosensor data appears to indicate an event worth analyzing in greater detail. Further, the biosensor device 110 is able to reduce power consumption by waiting until it detects a sufficiently significant arrhythmia event before sending any data to the smartphone 120.

Figure 2:
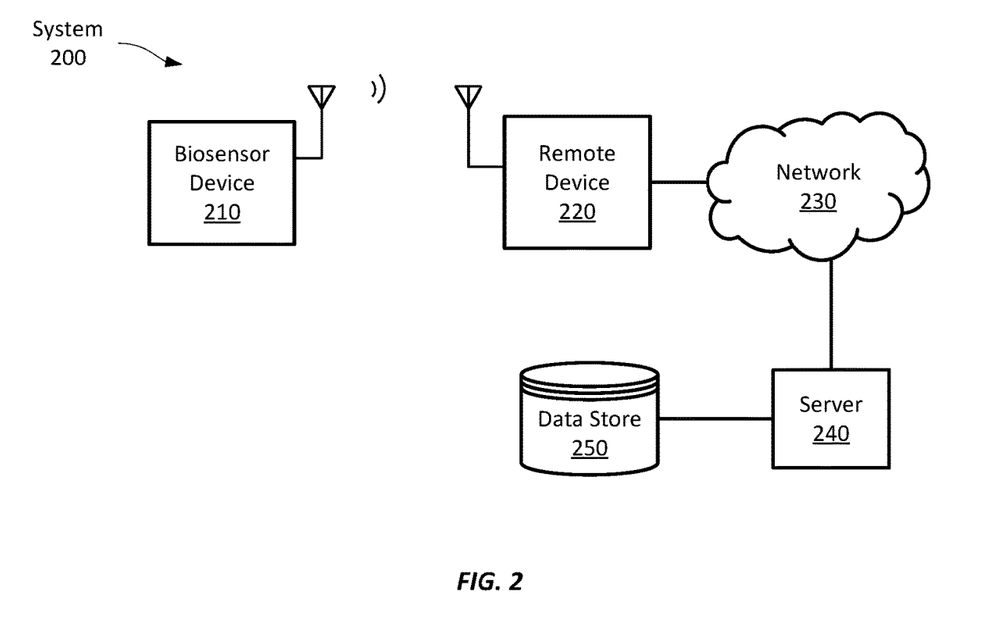

Referring now to FIG. 2, FIG. 2 shows an example system 200 that includes a wearable biosensor device 210 with adaptive power consumption. In this example, a wearable biosensor device 210 is illustrated as being capable of wireless communication with remote device 220. The remote device 220 is in turn in communication with a server 240 over one or more networks, consolidated as network 230. The server 240 is in communication with a data store 250.

The wearable biosensor device 210 may be any suitable wearable biosensor device. Examples include heart monitors (including electrocardiogram ("ECG") devices, pulse monitors, blood pressure monitors, etc.), continuous glucose monitors ("CGMs") or other analyte sensors, breathing monitors, etc. The wearable biosensor device 210 may include one or more biosensors, such as PPG sensors, ECG sensors, analyte sensors (invasive or non-invasive), galvanic skin response ("GSR") sensors, etc. Some types of sensors not designed as biosensors may be employed as biosensors in some examples. For example, an accelerometer may be not be designed as a biosensor, but may be employed to measure physiological parameters, such as chest movement (e.g., to detect breathing or cardiac movement) or activity (e.g., walking, sleeping, etc.) or physical activity. Thus, biosensors can include any type of sensor that has been adapted, e.g., by incorporation into a wearable biosensor device, to measure biological or physiological information. Further, such biosensors may be bodily incorporated within the wearable biosensor device 210 or may be external to the wearable biosensor device 210 and configured to communicate with the wearable biosensor device 210, e.g., via wired or wireless communications.

Some example wearable biosensor devices 210 are battery-powered, hermetically sealed devices that are designed to be worn by a person and discarded once the battery has been drained. They may be worn on any suitable location of the wearer's body, including on the chest, back, underarm areas, arms, legs, hands, feet, head, neck, etc. These example devices are hermetically sealed to prevent ingress of contaminants into the device, such as liquids, dust, etc. To help ensure the hermetic seal, some example wearable biosensor devices cannot be opened to replace the battery and thus have a useful life limited by the amount of power available from the battery. As the device is worn and performs its functions, it drains power from the battery until the battery is drained, at which time the device is discarded. To extend the battery life, and thus the useful life of the wearable biosensor device 210, the device 210 employs power management strategies as discussed in more detail herein. It should be appreciated that some wearable biosensor devices 210 may be dedicated to monitoring a specific physiological system in the wearer, such as the heart or lungs, but others may have multiple different kinds of sensors to monitor different physiological systems in the wearer.

The wearable biosensor device 210 receives sensor information or data from its one or more biosensors and performs processing on that data to detect potential events or other markers indicating data for further analysis. If an event or sufficient markers are identified, the wearable biosensor device 210 may then perform more processor-intensive processing on received or incoming sensor information or data. The results of such processing may then be stored in memory on the wearable biosensor device 210 or, if the urgency of the results are sufficiently high, the wearable biosensor device 210 can activate a radio subsystem to transmit the results, stored sensor data, wearer information, etc. to the remote device 220.

The remote device 220 may be any suitable computing device. For example, the remote device 220 may be a portable user device, such as a smartphone, smartwatch, tablet, laptop, etc. However, other types of remote devices 220 may be employed instead. For example, suitable remote devices 110 may be desktop or server computers or dedicated monitoring equipment, e.g., health monitoring equipment in a hospital or other medical facility. Communications between the wearable biosensor device 210 in this example employ BLE; however, any suitable wireless communications technique may be used, including those discussed below.

The remote device 220 in FIG. 2 is depicted as being communicatively coupled to a server 240 via network 230. While such connectivity may be desirable in some scenarios, examples according to this disclosure do not require that the remote device 220 be communicate with (or even able to communicate with) any device other than the biosensor device 210.

However, in examples where remote device 220 is capable of communicating with another device, such as server 240, it may employ any suitable wired or wireless communication mechanism, including Ethernet, Thunderbolt, Universal Serial Bus ("USB"), Bluetooth, BLE, any available 802.11 protocol, any suitable mesh networking protocol (e.g., 802.15.4, etc.), any cellular protocol (e.g., 4G, LTE, 5G, etc.), near-field communication ("NFC"), etc. Such communications may be through one or more intermediary networks, including any number of local area networks ("LANs"), wide area networks ("WANs"), metro-area networks ("MANs"), the Internet, etc.

The server 240 may be any suitable computing device capable of communicating with the remote device 220 and storing data received from the remote device 220 in the data store 250. While in this example, data store 250 is depicted as external to the server 240, the data store 250 may be implemented by the server 240 itself, such as through an internal database or storage device. Server 240 may receive information from the remove device 240 and perform additional analysis or processing on such information or store the information in the data store 250.

Figure 3:
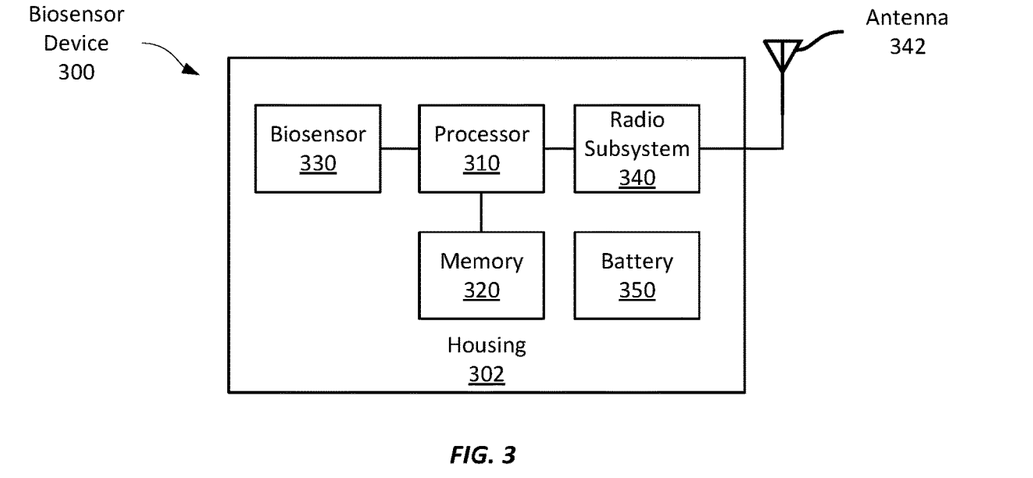
FIGS. 3-5 show example wearable biosensor devices with adaptive power consumption.

Referring now to FIG. 3, FIG. 3 illustrates an example wearable biosensor device 300 with adaptive power consumption. In this example, the biosensor device 300 includes a processor 310, memory 320, biosensor 330, and radio subsystem 340, which in turn includes an antenna 342. Each of these components 310-340 is powered by the battery 350. In this example, each of the components 310-350 are positioned within a hermetically sealed housing 302, though in some examples the biosensor 330 may include components that are positioned on the outside of the housing 302 or that protrude through the housing 302. In addition, the antenna 342 may be formed inside or outside the housing 302 and, in some examples, may be formed on the housing, whether on an inner or outer surface (or a combination of both).

The processor 310 in this example is a generally programmable microprocessor, but in some examples, the processor 310 may be any suitable microprocessor microcontroller, digital signal processor ("DSP"), or other programmable processor. Further, other examples of the device may use special purpose processors, including field-programmable gate arrays ("FPGAs") or application-specific integrated circuits ("ASICs") that have been specially configured to perform particular functionality without separate programming.

The biosensor 330 may be any suitable biosensor, as discussed above with respect to the biosensor 230 depicted in FIG. 2. And while this example only depicts the biosensor device 300 as including a single biosensor 330, any suitable number of biosensors may be included in other examples.

The radio subsystem 340 in this example includes a radio transceiver and an antenna 342 that are configured to operate according to BLE standards. However, any suitable radio subsystem may be employed, as discussed above with respect to FIG. 2. Further, the radio subsystem 340 in some examples, may only include a transmitter without a receiver. Some such embodiments may enable broadcasting of sensor information, while reducing power consumption by eliminating the need to receive radio transmissions.

Figure 4:
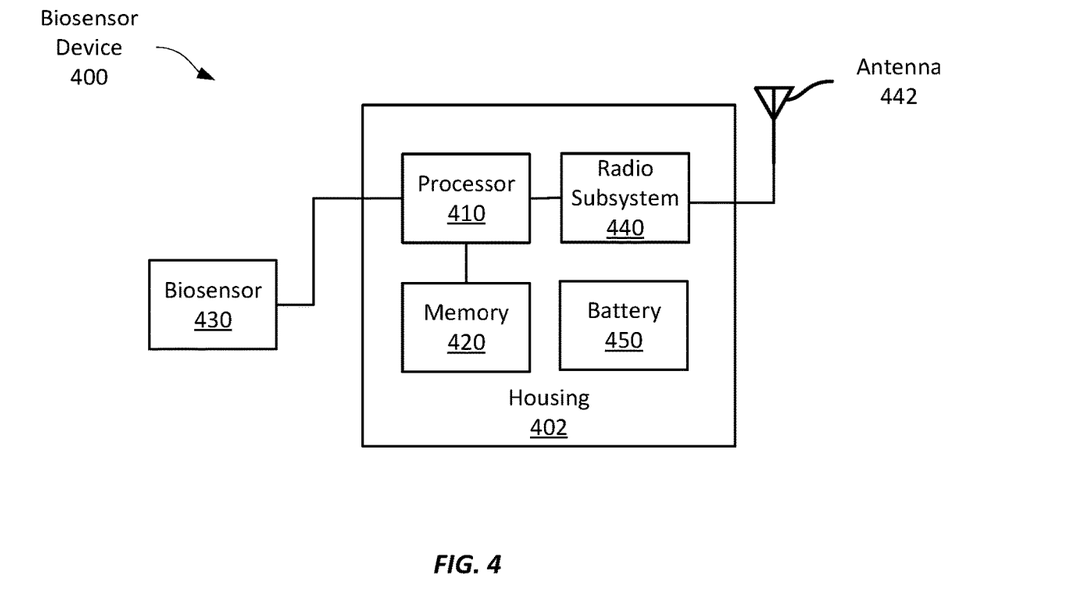

Referring now to FIG. 4, FIG. 4 shows another example wearable biosensor device 400. Similar to the example shown in FIG. 3, the biosensor device 400 includes a processor 410, memory 420, a biosensor 430, a radio subsystem 440, and a battery 450. In this example, however, the biosensor 430 is positioned outside of the device's housing 402, in which the other components 410, 420, 440, 450 are contained. Instead the biosensor 430 is positioned remotely on the wearer's body from the housing 402 and is communicatively coupled to the components in the housing 402 via a wired communications link. The type of wired communications link is selected based on the biosensor. For example, if the biosensor is an electrode, the wired communications link may include one or more wires to transmit voltage, current, or other analog signals generated by the electrode. However, if the biosensor outputs digital signals, the wired communications link may be configured according to any suitable serial or parallel communications protocol. And while this example shows only a single biosensor 430, the device 400 may include multiple biosensors 430, e.g., multiple ECG electrodes may be employed in some examples. Further, the device 400 may include biosensors 430 positioned both externally to the housing and internally to the housing (or on the housing or protruding through the housing).

Figure 5:
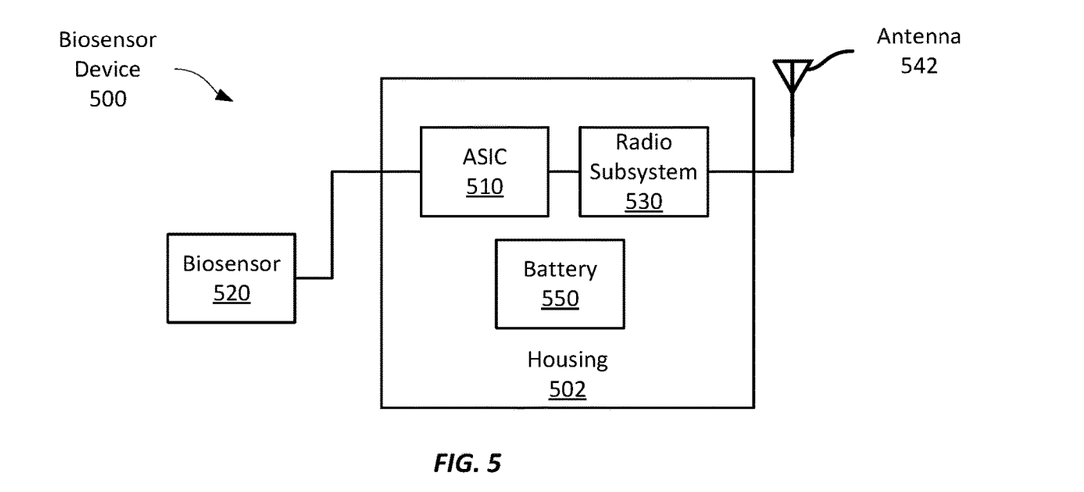

Referring now to FIG. 5, FIG. 5 shows another example wearable biosensor device 500. Similar to the example shown in FIG. 5, the biosensor device 500 includes a biosensor 530, a radio subsystem 540, and a battery 550, with the biosensor 530 positioned outside of the device's housing 502. In this example, however, the biosensor device 500 employs an ASIC 510 that does not have external memory. Instead, the ASIC 510 itself implements any programmatic elements in circuitry to process incoming sensor information. The sensor information and the processing results may then be stored within memory internal to the ASIC 510, or the ASIC may lack the memory to store such information and instead may store indicators of events of interest, e.g., flag values to indicate a cardiac event occurring. Alternatively, the device 500 may also include a separate memory device to store sensor information and processing results, but not programmatic instructions for the ASIC 510 to execute. And while in this example, the ASIC 510 is communicatively coupled to a biosensor 520 external to the housing 502, in some examples, the ASIC 510 may be communicatively coupled to a biosensor 520 positioned within or protruding through the housing.

Figure 6:
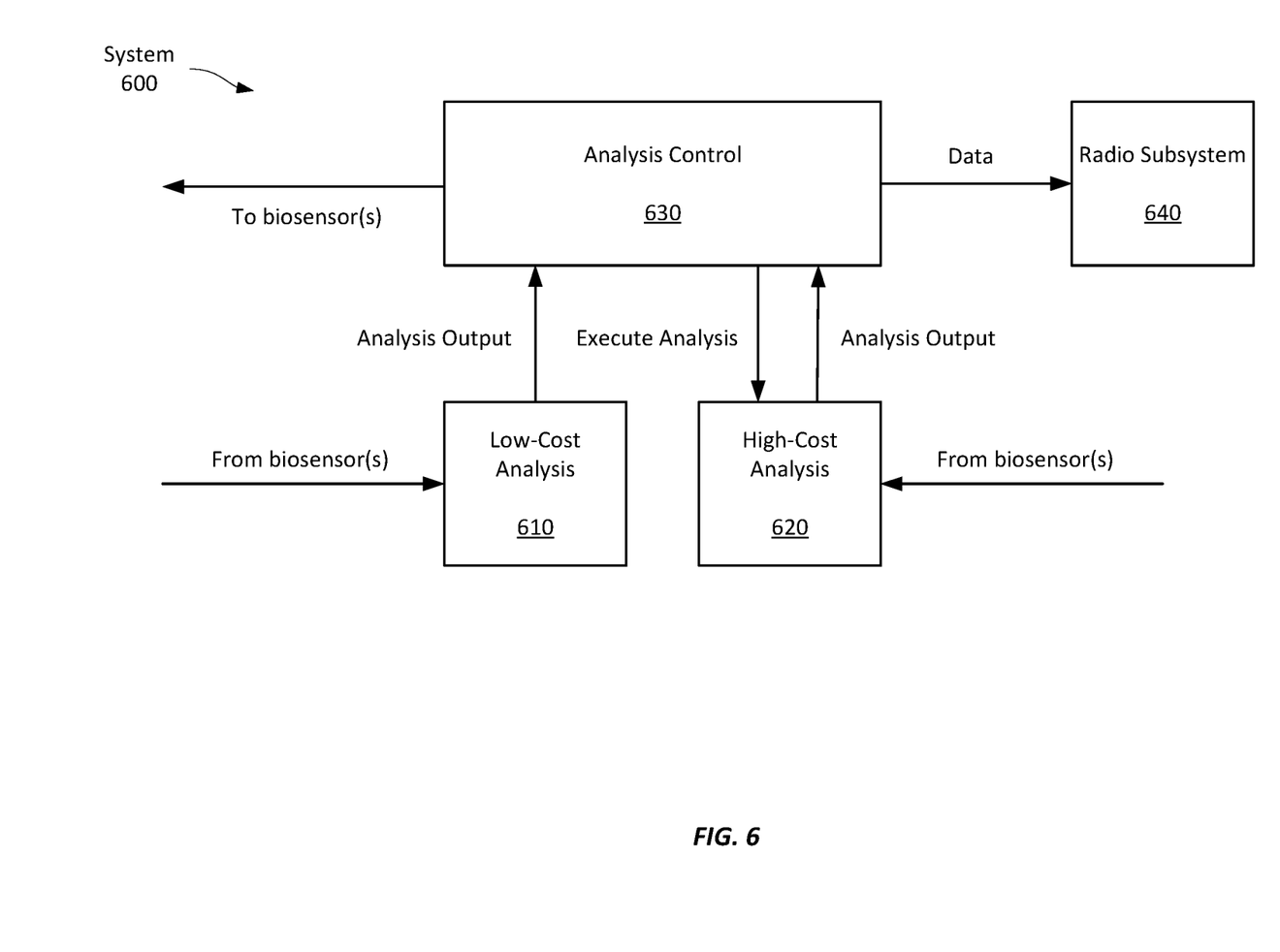
FIG. 6 shows an example logical flow diagram for wearable biosensor devices with adaptive power consumption.

Referring now to FIG. 6, FIG. 6 shows an example system's logical flow diagram for wearable biosensor devices with adaptive power consumption. The example system 600 will be discussed with respect to the system 200 described above with respect to FIG. 2. The example system 600 includes four components: low-cost analysis 610, high-cost analysis 620, analysis control 630, and radio subsystem 640. One of more of these components 610-640 may be implemented in software, circuitry, or a combination. Low-cost analysis 610 includes functionality that imposes relatively low power draw on the biosensor device's battery. The amount of power needed to execute the low-cost analysis 610 may vary according to the particular application, but since the low-cost analysis is intended to run regularly or continuously, its regular or continuous usage should still enable the device to have a useful life on the order of weeks or months before the battery is depleted. For example, low-cost analysis 610 may involve simple arithmetic calculations or comparisons, e.g., computing a pulse rate based on detected heartbeats over a period of time and comparing the pulse rate to a threshold.

In contrast, the high-cost analysis 620 includes functionality that imposes a significantly higher power draw than the low-cost analysis 610. For example, performing fast Fourier transform ("FFT") calculations on incoming sensor data is computationally expensive and therefore involves significant processor utilization and, consequently, power consumption. Performing the high-cost analysis 620 on a regular basis would significantly reduce the useful life of the wearable sensor device, e.g., from weeks or months to a few days.

Examples of low-cost analysis 610 include detecting whether the wearer is idle or active, e.g., sleeping or awake (which can be determined based on determining whether accelerometer data includes values above a threshold for at least a predetermined period of time), determining a pulse rate or pulse width, determining a breathing rate, determining whether temperature data exceeds a threshold, determining whether glucose (or another analyte) is below (or above) a threshold value. Such analyses involve a few, basic arithmetic computations and can be readily completed in relatively few processor clock cycles, resulting in low processor utilization (e.g., <5-10%) in steady-state operation.

Examples of high-cost analysis 620 include computing movement data, e.g., step count, gait, energy expenditure, ECG signal processing (e.g., determining P, Q, R, S, T, and/or U wave information), PPG signal processing to estimate blood pressure based on pulse wave transit time, etc. Such processing involves complex mathematical processing, processing large quantities of data, or both. As a result, high-cost analysis can cause high processor utilization while active, e.g., >90% utilization. Even short periods of such high processor utilization, e.g., 50 ms, can rapidly drain a battery if it is repeated frequently.

It should be appreciated that while this example system 600 shows only a single block for low-cost analysis 610 and a single block for high-cost analysis 610, it should be appreciated that some example systems may include multiple different low-cost or high-costs analysis components. For example a wearable biosensor device 210 may include multiple biosensors, each providing sensor information about different physiological aspect of the wearer. The wearable biosensor device 210 may then employ different low-cost analysis for each different type of sensor information and, similarly, employ different high-cost analysis for each different type of sensor information. Further, depending on the particular implementation, multiple sensors may target the same physiological aspect of the wearer. For example, a biosensor device may include both a PPG sensor and ECG electrodes to measure cardiac activity. The biosensor device may then perform low-cost analysis based on PPG information and high-cost analysis based on ECG information in the event the PPG information indicates an irregularity. Still further permutations of sensors, low-cost analysis, and high-cost analysis are contemplated by this disclosure.

In addition to the analysis components 610, 620, the system 600 includes an analysis control component 630, which manages which analysis functionality is activated as well as whether the radio subsystem 640 should be activated or not. In this example, the analysis control component 630 controls the activation and deactivation of the high-cost analysis component 620 based on information received from the low-cost analysis component 610. As discussed above, the low-cost analysis component 610 executes regularly, e.g., at regular intervals, or continuously and processes biosensor information received from the biosensor(s). The low-cost analysis component 610 outputs results based on its analysis of the sensor information. The analysis output can be values generated by the low-cost analysis, e.g., pulse rate, detected movement, temperature, etc. In some examples, the analysis output from the low-cost analysis component 610 can be flag or state information, such as "awake," "asleep," "normal heart rate," "normal breathing rate," etc. Such information may be generated based on the low-cost analysis determining, e.g., the wearer's pulse rate and comparing it to one or more thresholds to identify a corresponding state.

After receiving the analysis output, the analysis control component 630 may determine whether to activate the high-cost analysis component 620. To do so, the analysis control component 630 may determine whether the low-cost analysis indicates an abnormal event or condition. For example, if PPG sensor data indicates an erratic pulse rate or arrhythmia, the analysis control component 630 may determine whether the pulse rate or arrhythmia satisfies one or more conditions, e.g., duration of the event, deviation from a normal pulse rate or rhythm, number of occurrences during a predetermined interval, etc. If sufficient conditions are satisfied, the analysis control component 630 activates the high-cost analysis component 620. This may be implemented by calling an entry function for the high-cost analysis component 620 or launching a separate software process that implements the high-cost analysis component 620. The high-cost analysis component 620 may then perform its analysis and return the results to the analysis control component 630. In this example, after the high-cost analysis component 620 has performed its analysis, it is deactivated. This may result from one or more functions completing and not being re-executed or the separate process terminating.

In some examples, in addition to activating the high-cost analysis component 620, the analysis control 630 may modify modes of operation of one or more biosensors. For example, the low-cost analysis component 610 may only require low-resolution data from the biosensor, e.g., it may need 10 samples per second or 8-bit data samples, during steady-state operation. However, the high-cost analysis component 620 may require high-resolution data, e.g., a 1000 Hz sampling rate or 12- or 16-bit data samples. After determining to activate the high-cost analysis component 620, the analysis control component 630 may determine corresponding biosensor operational parameters and transmit one or more signals to the biosensor to adjust its mode of operation to conform to the determined operational parameters, e.g., by changing sampling rate, data precision, etc. After the high-cost analysis component 620 has completed its analysis, the analysis control component 630 may change the biosensors mode of operation back to its steady-state configuration.

In addition to determining whether to activate the high-cost analysis component 620, the analysis control component 630 may also determine whether to activate the radio subsystem 640 to transmit information to a remote device 220. The analysis control component 630 may determine to activate the radio subsystem 640 based on analysis output from the low-cost analysis component 610 without activating the high-cost analysis component 620. For example, the low-cost analysis component 610 may output information indicating an abnormal event or condition, such as discussed above. The analysis control 630 may be configured to then activate the radio subsystem 640 to transmit sensor data from the wearable biosensor device 210 to the remote device 220 for analysis, rather than activating the high-cost analysis component 620. Further, in some examples, the wearable biosensor device 210 may not include a high-cost analysis component 620 and may instead rely on the remote device 220 or server 240 to perform complex analysis of biosensor data or information that has been transmitted from the biosensor device 210.

In some examples, the analysis control component 630 may determine to activate the radio subsystem 640 based on analysis output from the high-cost analysis component 620. For example, the analysis control component 630 may receive the analysis output from the high-cost analysis component 620 and determine whether the analysis output satisfies one or more criteria to activate the radio subsystem. In an example where the high-cost analysis component 620 analyzes ECG or PPG sensor information to identify potentially dangerous cardiac events, the analysis control component 630 may determine whether the results of analysis indicate a sufficiently urgent cardiac event or condition, e.g., atrial fibrillation, ventricular tachycardia, etc. to transmit information to the remote device 220, e.g., to alert the wearer, a family member, or a medical professional.

If the analysis control component 630 activates the radio subsystem 640, it activates a radio transmitter (and receiver, if appropriate) and transmits information to the remote device 220. The information may include one or more of the results of the high-cost analysis, results of the low-cost analysis, raw sensor information, detected events or conditions, etc. After the information has been transmitted, the radio subsystem 640 is deactivated to reduce power consumption.

While the system 600 described with respect to FIG. 6 includes one each of an analysis control component 630, a low-cost analysis component 610, and a high-cost analysis component 630, some example systems may include more than one of one or more of such components 610-630. For example, in a wearable biosensor device having multiple biosensors, multiple low- or high-cost analysis components may be included. Further, different analysis control components 630 may be employed to manage different low- and high-cost analysis components. Still further variations are contemplated within the scope of this disclosure.

Figure 7:
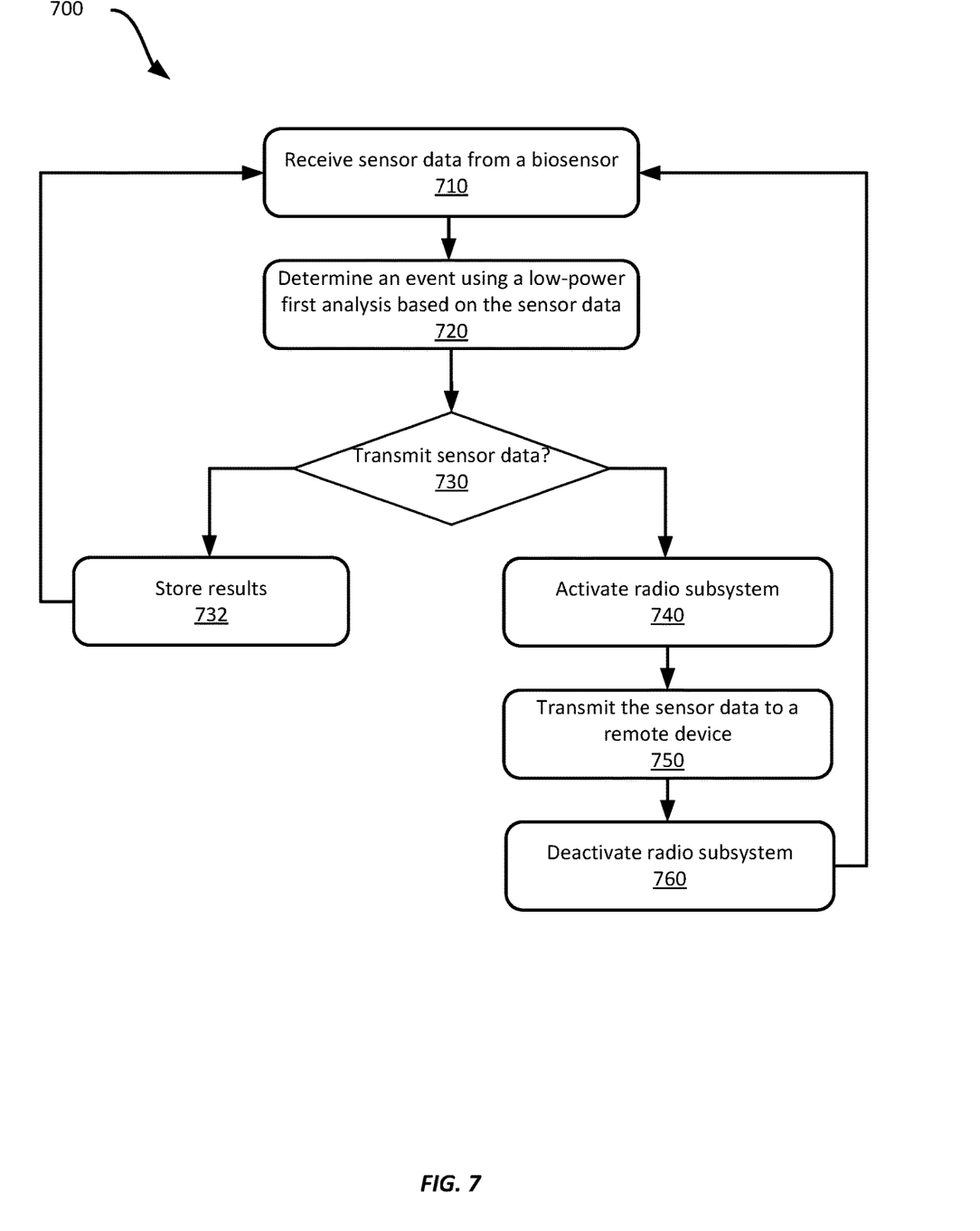
FIGS. 7-8 shows a flowchart for an example method for wearable biosensor devices with adaptive power consumption.

Referring now to FIG. 7, FIG. 7 shows a flowchart for an example method 700 for wearable biosensor devices with adaptive power consumption. The example method 700 will be discussed with respect to the system 200 shown in FIG. 2 and the data flow diagram shown in FIG. 6; however any suitable system according to this disclosure may be employed.

At block 710, the wearable biosensor device 210 receives sensor data from a biosensor. As discussed with respect to FIGS. 1-5, biosensor devices may include or be communicatively coupled to one or more biosensors that measure physiological parameters of the wearer. The biosensor device's processor receives the sensor signals from the one or more biosensors and extracts sensor data from those signals.

At block 720, the wearable biosensor device 210 determines an event using an analysis based on the sensor data. As discussed above with respect to FIG. 6, low-cost analysis component 610 processes received sensor data and outputs the results of the analysis, which may include numeric values (e.g., pulse rate of 65 beats per minute), flag values (e.g., awake, asleep), events (e.g., arrhythmia, elevated temperature), etc. Thus, determining the event may include determining any of the foregoing.

At block 730, the biosensor device 210 determines whether to transmit the sensor data to a remote device. In this example, the biosensor device 210 determines whether the event is sufficiently urgent to warrant reporting the sensor data. For example, the analysis control component 630 may receive a pulse rate or change in wearer waking state, and determine whether one or more criteria have been satisfied. If the one or more criteria have been satisfied, the analysis control component 630 determines to transmit the sensor data to a remote device and the method 700 proceeds to block 740. Otherwise, the method 700 proceeds to block 732.

At block 732, biosensor device 210 stores the sensor data or analysis output from the low-cost analysis component 610, and the method 700 returns to block 710.

At block 740, the biosensor device 210 activates the radio subsystem 640. In this example, the biosensor device 210 activates a BLE transceiver; however, in other examples, biosensor devices may employ any suitable wireless transmitter or transceiver and may activate such wireless transmitter or transceiver.

At block 750, the biosensor device 210 transmits sensor data or other information to the remote device 220 using the radio subsystem 640.

At block 760, the biosensor device 210 deactivates the radio subsystem 640 and the method returns to block 710.

Figure 8:
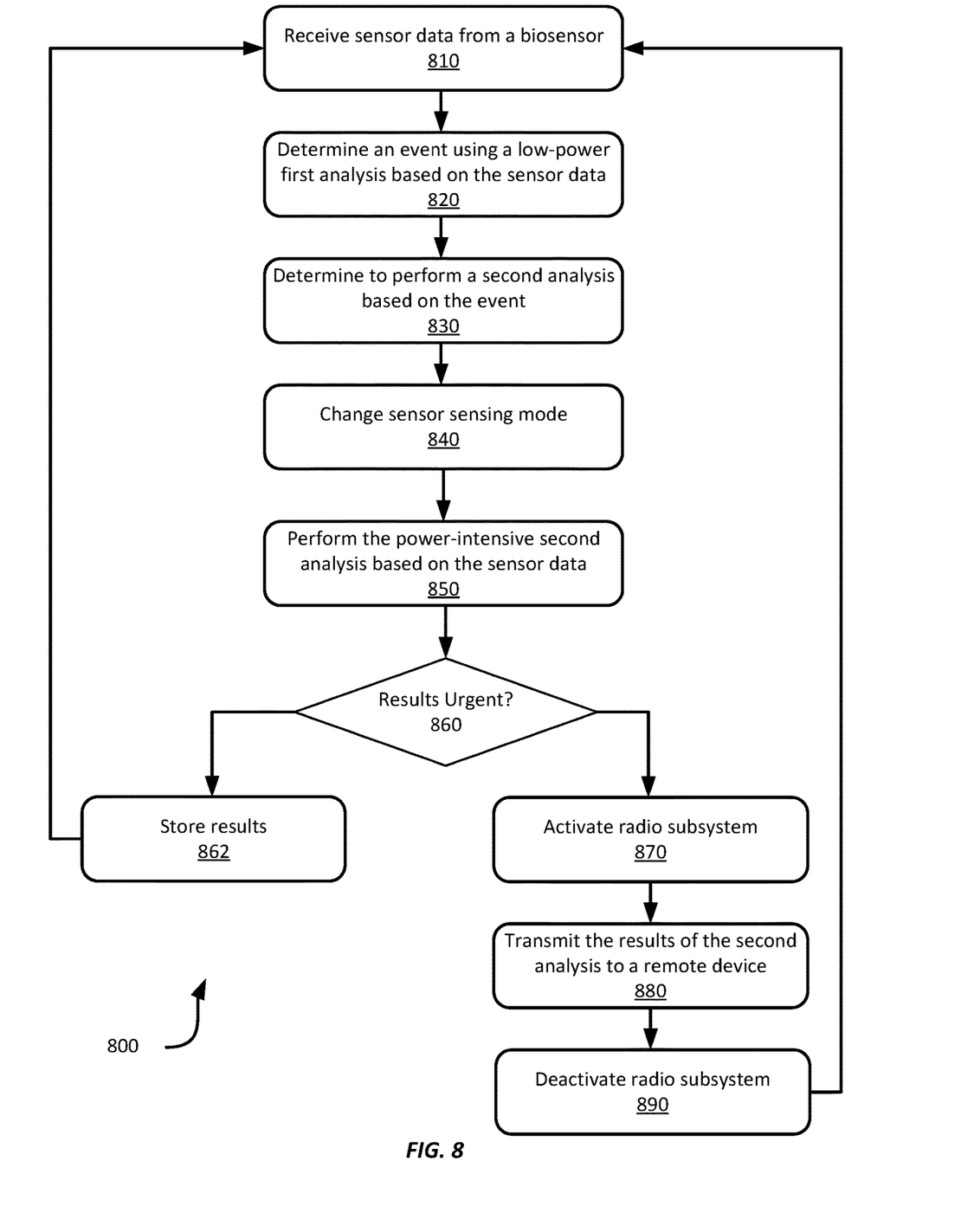

Referring now to FIG. 8, FIG. 8 shows a flowchart for an example method 800 for wearable biosensor devices with adaptive power consumption. The example method 800 will be discussed with respect to the system 200 shown in FIG. 2 and the data flow diagram shown in FIG. 6; however any suitable system according to this disclosure may be employed.

At block 810, the biosensor device 210 receives sensor data from one or more biosensors generally as discussed above with respect to block 710.

At block 820, the biosensor device 210 determines an event using a first analysis based on the sensor data, the first analysis having a first power cost generally as described above with respect to block 720 and the low-cost analysis component 610.

At block 830, the biosensor device 210 determines to perform a second analysis based on the determined event generally as discussed above with respect to the analysis control component 630 and FIG. 6.

At block 840, the biosensor device 210 changes a mode of operation for one or more biosensors generally as discussed above with respect to the analysis control component 630 and FIG. 6. It should be understood that in some examples, block 840 may be omitted.

At block 850, the biosensor device 210 performs a second analysis based on the sensor data, the second analysis having a second power cost greater than the first power cost generally as discussed above with respect to the high-cost analysis component 620 and FIG. 6.

At block 860, the biosensor device 210 determines whether the analysis output of the second analysis is sufficiently urgent generally as discussed above with respect to analysis control component 630 and FIG. 6. If the results are sufficiently urgent, the method 800 proceeds to block 870; otherwise, the method proceeds to block 862.

At block 862, the biosensor device 210 stores the analysis output from the high-cost analysis component 630 and the method 800 returns to block 810.

At block 870, the biosensor device 210 activates the radio subsystem 870 generally as discussed above with respect to block 740.

At block 880, the biosensor device 210 transmits the results of the second analysis to the remote device 220 using the radio subsystem generally as discussed above with respect to block 750.

At block 890, the biosensor device deactivates the radio subsystem generally as discussed above with respect to block 760 and the method 800 returns to block 810.

Figure 9:
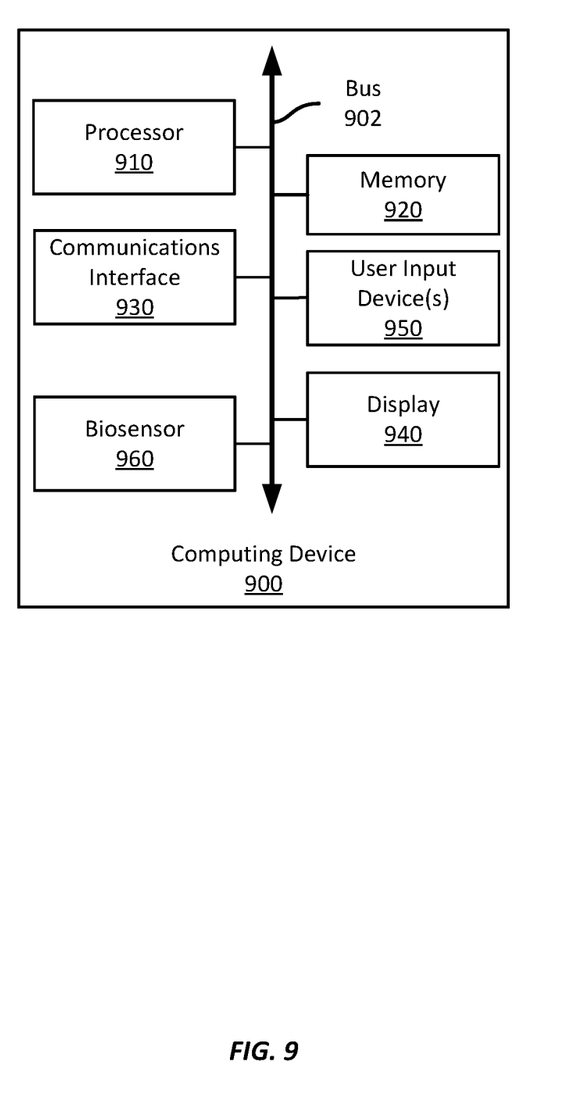
FIG. 9 shows an example computing device suitable for use with wearable biosensor devices with adaptive power consumption.

Referring now to FIG. 9, FIG. 9 shows an example computing device 900 suitable for use in example wearable biosensor devices with adaptive power consumption according to this disclosure. The example computing device 900 includes a processor 910 which is in communication with the memory 920 and other components of the computing device 900 using one or more communications buses 902. The processor 910 is configured to execute processor-executable instructions stored in the memory 920 to perform one or more methods for wearable biosensor devices with adaptive power consumption according to different examples, such as part or all of the example methods 700, 800 described above with respect to FIGS. 7 and 8. The computing device, in this example, also includes one or more user input devices 950, such as a keyboard, mouse, touchscreen, microphone, etc., to accept user input. The computing device 900 also includes a display 940 to provide visual output to a user.

The computing device 900 also includes a communications interface 940. In some examples, the communications interface 930 may enable communications using one or more networks, including a local area network ("LAN");

wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   receiving sensor data from a biosensor;
   determining an event using a first analysis based on the sensor data, the first analysis having a first computational complexity and a first power cost;
   determining to perform a second analysis based on the event;
   in response to determining to perform the second analysis, performing the second analysis based on second sensor data received from the biosensor, the second analysis having a second computational complexity greater than the first computational complexity and having a second power cost greater than the first power cost; and
   wirelessly transmitting results of the second analysis to a remote device.

2. The method of claim 1, further comprising:
   determining an urgency of the results of the second analysis;
   in response to determining that the urgency meets or exceeds a threshold, activating a radio subsystem; and
   wherein the wirelessly transmitting occurs in response to determining the urgency meets or exceeds the threshold, the wirelessly transmitting using the radio subsystem.

3. The method of claim 2, further comprising deactivating the radio subsystem after the wirelessly transmitting the results to the remote device completes.

4. The method of claim 2, wherein the radio subsystem comprises a Bluetooth transceiver.

5. The method of claim 1, further comprising:
   in response to determining to perform the second analysis:
      changing a mode of operation of the biosensor from a first resolution to a second resolution, the second resolution higher than the first resolution;
      receiving high-resolution sensor data; and
      wherein the second sensor data comprises the high-resolution sensor data.

6. The method of claim 5, further comprising, after completing the second analysis, changing the mode of operation of the biosensor to the first resolution from the second resolution.

7. The method of claim 6, wherein the first resolution comprises a first sampling rate and the second resolution comprises a second sampling rate, the second sampling rate higher than the first sampling rate.

8. The method of claim 1, wherein the biosensor comprises a temperature sensor, a pulse sensor, an $SpO_2$ sensor, a blood pressure sensor, or an accelerometer.

9. The method of claim 1, further comprising storing the first or second sensor data.

10. A device comprising:
    a biosensor;
    a radio subsystem;
    a non-transitory computer-readable medium; and a processor communicatively coupled to the biosensor, the radio subsystem, and the non-transitory computer-readable medium, the processor configured to execute processor-executable instructions stored in the non-transitory computer-readable medium to:
receive first sensor data from a biosensor;
determine an event using a first analysis based on the sensor data, the first analysis having a first computational complexity and a first power cost;
determine to perform a second analysis based on the event;
in response to a determination to perform the second analysis, perform the second analysis based on second sensor data received from the biosensor, the second analysis having a second computational complexity greater than the first computational complexity and having a second power cost greater than the first power cost; and
wirelessly transmit, using the radio subsystem, results of the second analysis to a remote device.

11. The device of claim 10, wherein the processor is further configured to execute processor-executable instructions stored in the non-transitory computer-readable medium to:
determine an urgency of the results of the second analysis;
in response to a determination that the urgency meets or exceeds a threshold, activate the radio subsystem; and
wherein the wirelessly transmitting occurs in response to determining the urgency meets or exceeds the threshold, the wireless transmitting using the radio subsystem.

12. The device of claim 11, wherein the processor is further configured to execute processor-executable instructions stored in the non-transitory computer-readable medium to deactivate the radio subsystem after the wirelessly transmitting the results to the remote device completes.

13. The device of any of claim 11, wherein the radio subsystem comprises a Bluetooth transceiver.

14. The device of claim 10, wherein the processor is further configured to execute processor-executable instructions stored in the non-transitory computer-readable medium to:
in response to a determination to perform the second analysis:
change a mode of operation of the biosensor from a first resolution to a second resolution, the second resolution higher than the first resolution;
receive high-resolution sensor data; and
wherein the second sensor data comprises the high-resolution sensor data.

15. The device of claim 14, wherein the processor is further configured to execute processor-executable instructions stored in the non-transitory computer-readable medium to, after completing the second analysis, change the mode of operation of the biosensor to the first resolution from the second resolution.

16. The device of claim 15, wherein the first resolution comprises a first sampling rate and the second resolution comprises a second sampling rate, the second sampling rate higher than the first sampling rate.

17. The device of claim 10, wherein the biosensor comprises a temperature sensor, a pulse sensor, an SpO$_2$ sensor, a blood pressure sensor, or an accelerometer.

18. The device of claim 10, wherein the processor is further configured to execute processor-executable instructions stored in the non-transitory computer-readable medium to store the sensor data in the non-transitory computer-readable medium.

19. A non-transitory computer-readable medium comprising processor executable instructions configured to cause a processor to:
receive first sensor data from a biosensor;
determine an event using a first analysis based on the first sensor data, the first analysis having a first computational complexity and a first power cost;
determine to perform a second analysis based on the event;
in response to a determination to perform the second analysis, perform the second analysis based on second sensor data received from the biosensor, the second analysis having a second computational complexity greater than the first computational complexity and having a second power cost greater than the first power cost; and
wirelessly transmit results of the second analysis to a remote device.

20. The non-transitory computer-readable medium of claim 19, wherein the processor is further configured to execute processor-executable instructions stored in the non-transitory computer-readable medium to:
determine an urgency of the results of the second analysis;
in response to a determination that the urgency meets or exceeds a threshold, activate a radio subsystem; and
wherein the wirelessly transmitting occurs in response to determining the urgency meets or exceeds the threshold, the wireless transmitting using the radio subsystem.

21. The non-transitory computer-readable medium of claim 20, wherein the processor is further configured to execute processor-executable instructions stored in the non-transitory computer-readable medium to deactivate the radio subsystem after the wirelessly transmitting the results to the remote device completes.

22. The non-transitory computer-readable medium of claim 20, wherein the radio subsystem comprises a Bluetooth transceiver.

23. The non-transitory computer-readable medium of claim 19, wherein the processor is further configured to execute processor-executable instructions stored in the non-transitory computer-readable medium to:
in response to a determination to perform the second analysis:
change a mode of operation of the biosensor from a first resolution to a second resolution, the second resolution higher than the first resolution;
receive high-resolution sensor data; and
wherein the second sensor data comprises the high-resolution sensor data.

24. The non-transitory computer-readable medium of claim 14, wherein the processor is further configured to execute processor-executable instructions stored in the non-transitory computer-readable medium to, after completing the second analysis, change the mode of operation of the biosensor to the first resolution from the second resolution.

25. The non-transitory computer-readable medium of claim 15, wherein the first resolution comprises a first sampling rate and the second resolution comprises a second sampling rate, the second sampling rate higher than the first sampling rate.

26. The non-transitory computer-readable medium of claim 19, wherein the biosensor comprises a temperature sensor, a pulse sensor, an $SpO_2$ sensor, a blood pressure sensor, or an accelerometer.

27. The non-transitory computer-readable medium of any of claim 19, wherein the processor is further configured to execute processor-executable instructions stored in the non-transitory computer-readable medium to store the first or second sensor data in a non-transitory computer-readable medium.

* * * * *

UNITED STATES PATENT AND TRADEMARK OFFICE
CERTIFICATE OF CORRECTION

| | | |
|---|---|---|
| PATENT NO. | : 12,364,400 B2 | Page 1 of 1 |
| APPLICATION NO. | : 17/457504 | |
| DATED | : July 22, 2025 | |
| INVENTOR(S) | : Charles Nicholson, David He and Brian Schiffer | |

It is certified that error appears in the above-identified patent and that said Letters Patent is hereby corrected as shown below:

In the Claims

In Column 14, Claim 1, Lines 15-18, "receiving sensor data from a biosensor;
determining an event using a first analysis based on the sensor data, the first analysis having a first computational complexity and a first power cost;"
Should be changed to --receiving first sensor data from a biosensor;
determining an event using a first analysis based on the first sensor data, the first analysis having a first computational complexity and a first power cost;--

In Column 15, Claim 10, Lines 6-9, "receive first sensor data from a biosensor;
determine an event using a first analysis based on the sensor data, the first analysis having a first computational complexity and a first power cost;"
Should be changed to --receive first sensor data from the biosensor;
determine an event using a first analysis based on the first sensor data, the first analysis having a first computational complexity and a first power cost;--

Signed and Sealed this
Second Day of September, 2025

Coke Morgan Stewart
*Acting Director of the United States Patent and Trademark Office*